United States Patent [19]
Wells

[11] Patent Number: 4,576,110
[45] Date of Patent: Mar. 18, 1986

[54] ROTOR HAVING A CHAMBER BLOCK WITH AN ABSORBANT PLUG

[75] Inventor: John R. Wells, Culver City, Calif.

[73] Assignee: E. I. Du Pont de Nemours and Company, Wilmington, Del.

[21] Appl. No.: 496,099

[22] Filed: May 19, 1983

[51] Int. Cl.[4] ............................................. B05C 11/08
[52] U.S. Cl. ...................................... 118/52; 118/412
[58] Field of Search ................... 118/52, 53, 54, 407, 118/412; 427/2, 240

[56] References Cited

U.S. PATENT DOCUMENTS

| | | | |
|---|---|---|---|
| 3,705,048 | 12/1972 | Staunton | 117/3 |
| 3,870,014 | 5/1973 | Buck | 118/52 |
| 4,103,643 | 8/1978 | Staunton | 118/50 |
| 4,108,109 | 8/1978 | Barger et al. | 118/52 |
| 4,197,329 | 5/1980 | Holroyd et al. | 427/2 |
| 4,241,005 | 12/1980 | Rothschild et al. | 264/311 |
| 4,244,916 | 1/1981 | Guigan | 422/72 |
| 4,250,830 | 2/1981 | Leif | 118/52 |
| 4,314,523 | 2/1982 | Boeckel et al. | 118/50 |
| 4,327,661 | 5/1982 | Boeckel | 118/52 |
| 4,391,710 | 5/1983 | Gordon | 210/361 |
| 4,423,699 | 1/1984 | Boeckel et al. | 118/52 |

OTHER PUBLICATIONS

Watson, A Slide Centrifuge: An Apparatus for Concentrating Cells in Suspension onto a Microscope Slide, The Journal of Laboratory and Clinical Medicine, vol. 68, No. 3, pp. 494-501, Sep. 1966.
"A Device for Preparing Cell Spreads", Dore & Balfour, Immunology, 1965, vol. 9, pp. 403-405.

Primary Examiner—John P. McIntosh

[57] ABSTRACT

A chamber block for a centrifuge is provided with an inlet orifice, inlet channel, outlet channel and outlet orifice through which a sample of cells and supernatant may be centrifuged onto a deposition surface. The chamber block includes a recess sized to receive a plug of an absorbent material which withdraws excess supernatant from the deposition surface.

18 Claims, 10 Drawing Figures

U.S. Patent   Mar. 18, 1986   Sheet 1 of 3   4,576,110
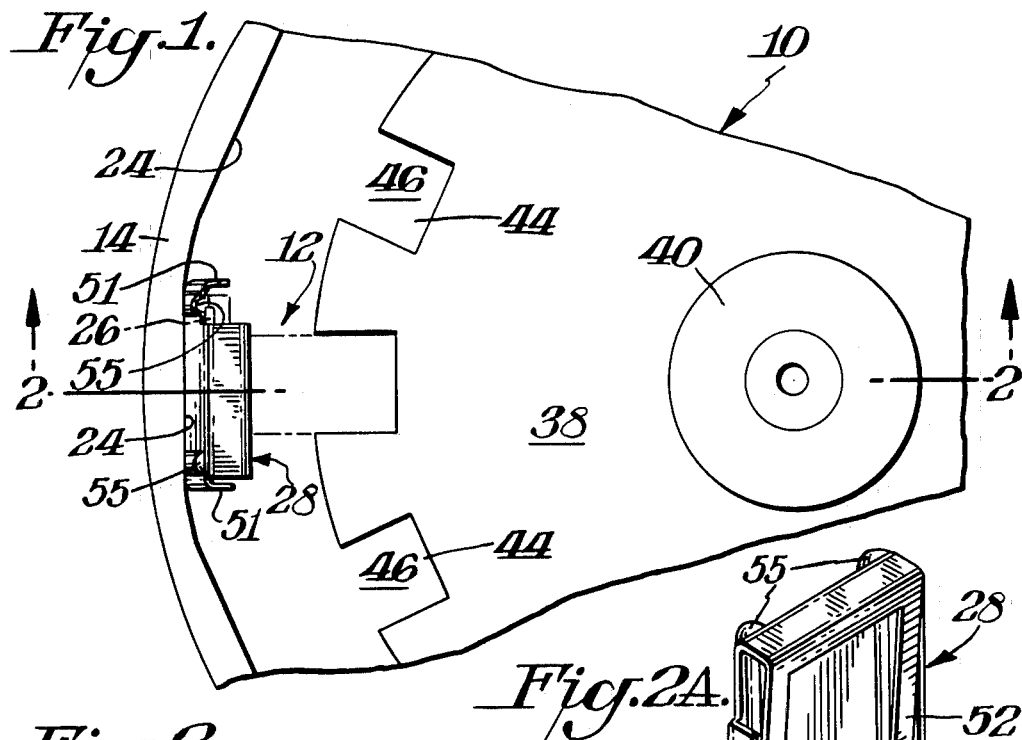
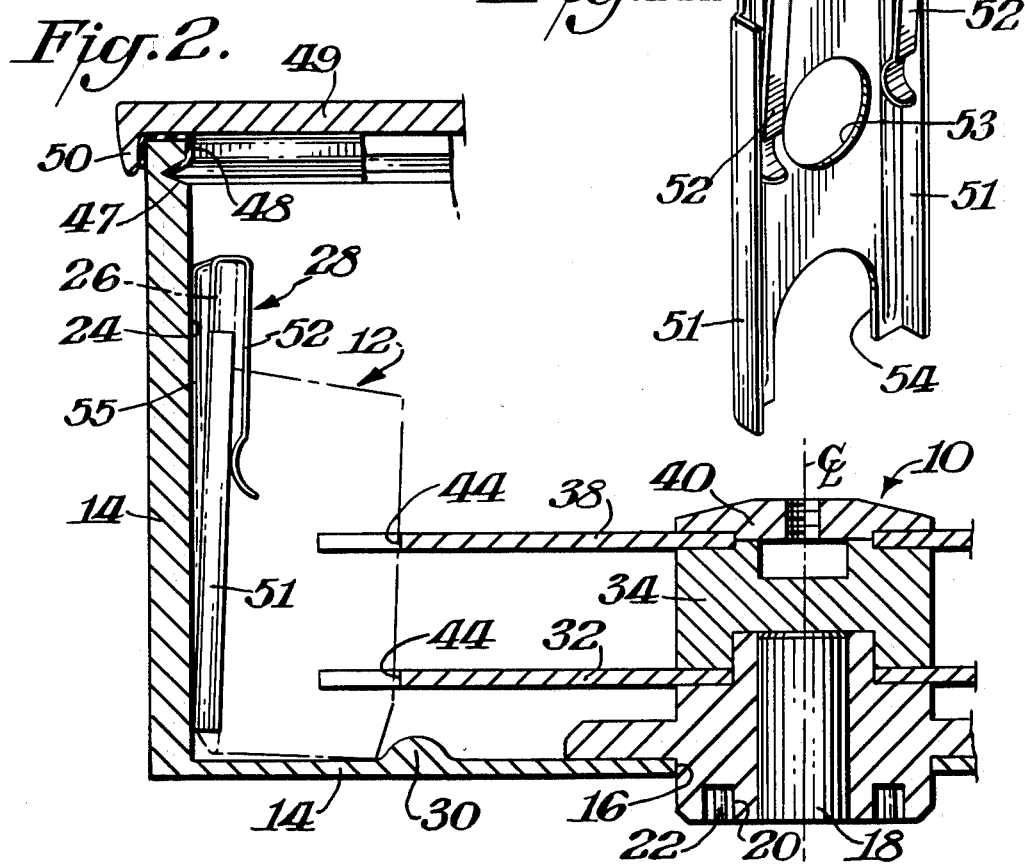

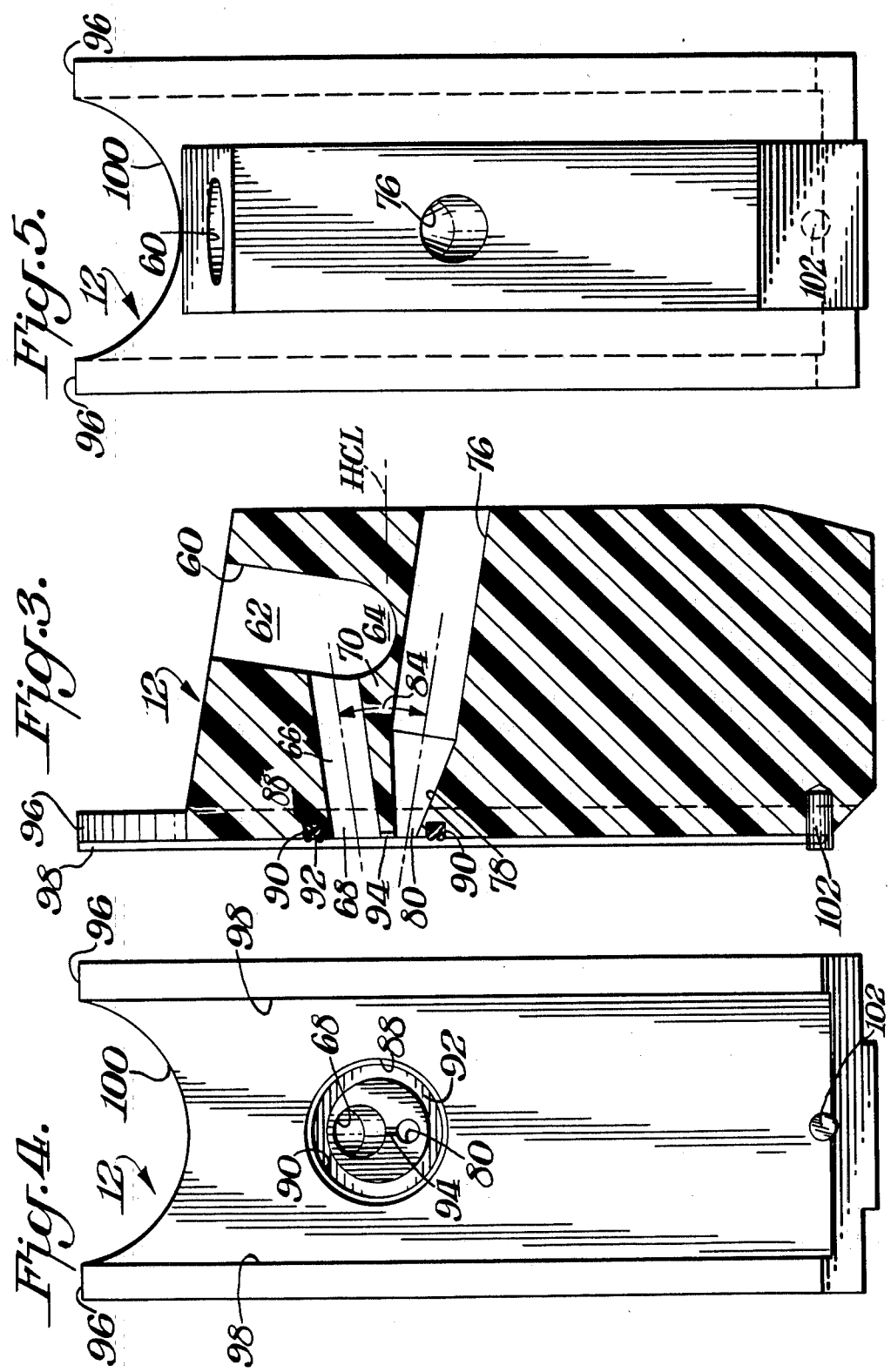

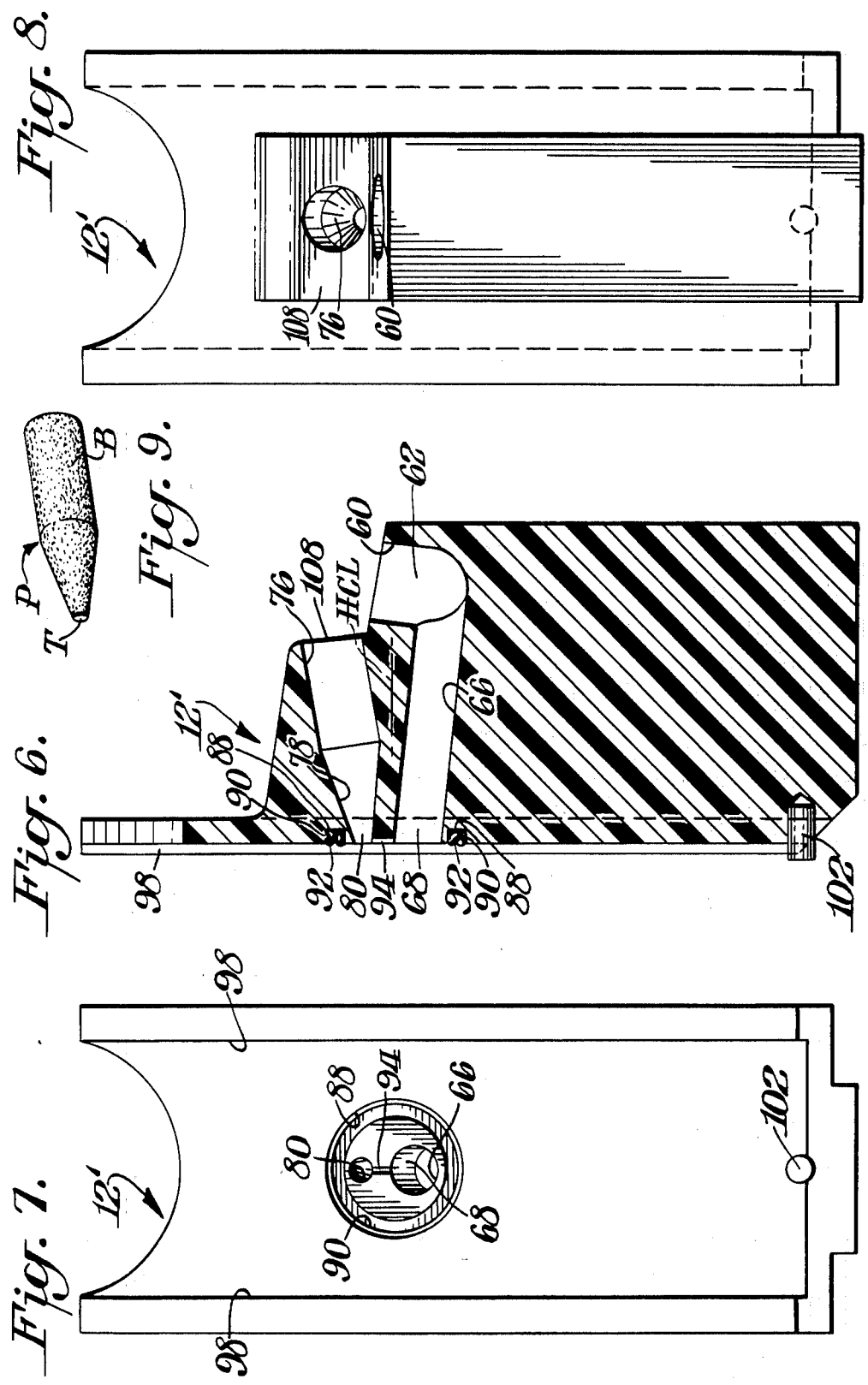

ROTOR HAVING A CHAMBER BLOCK WITH AN ABSORBANT PLUG

BACKGROUND OF THE INVENTION

This invention relates to a centrifuge rotor of the type adapted to deposit particles suspended within a supernatant onto a deposition surface and, in particular, to a chamber block for such a rotor having a recess provided therein adapted to receive an absorbant plug.

The centrifuge rotor arrangement such as that described in U.S. Pat. No. 4,423,699 and in U.S. Pat. No. 4,314,523, both assigned to the assignee of the present invention is adapted to deposit, or sediment, particles, such as blood cells, suspended in a liquid medium known as a supernatant onto a suitable deposition surface, such as a microscope slide, so that further examination of the cells may occur.

Each rotor arrangement is adapted to receive a plurality of removable chamber blocks therein. Each chamber block is provided with an inlet orifice communicating with an inlet channel for receiving a sample containing a supernatant having particles suspended therein and an outlet channel through which the particles and supernatant are moved under the influence of centrifugal force toward the deposition surface. A supernatant withdrawal conduit, or cannula, extends through the body of the chamber block. Supernatant is collected by withdrawing the same under suction in a direction rearwardly from the deposition surface. Exemplary of chamber blocks usable with the rotors having a vacuum source incorporated therewith are those described and claimed in U.S. Pat. No. 4,306,514 (Bouclier) and U.S. Pat. No. 4,327,661 (Boeckel).

Other techniques are known in the art for withdrawing excess supernatant from the vicinity of the deposition surface. For example, a device sold under the name of "Cytospin" by Shandon Elliott utilizes a bowl-type centrifuge rotor whose outer periphery defines a vertical wall adapted to receive microscope slides. Chambers for holding samples to be sedimented are positioned radially against the slides with a piece of filter paper disposed between each chamber and its associated slide. A hole in the filter paper is positioned over the outlet orifice of the chamber such that cells and the supernatant when centrifuged are driven against the slides. Capillary force of the filter paper and centrifugal force facilitate the withdrawal of excess fluid from the surface of the slide by forcing the excess liquid into the filter paper. Unfortunately, however, the filter paper can have a deleterious effect in that it tends to absorb the fluid so rapidly cells are literally "sucked" into the peripheral edges of the filter paper surrounding the outlet orifice with relatively few cells having sufficient time to pellet or sediment against the slide itself. For this reason the cells tend to run dry.

Accordingly, it would be desirable to provide a chamber block for use with a centrifuge rotor of the type for sedimenting cells against the deposition surface that avoids the use of filter paper between the chamber block and the deposition surface and the use of suction to withdraw the supernatant rearwardly from the deposition surface.

SUMMARY OF THE INVENTION

The instant invention relates to a chamber block for use in a centrifuge adapted to sediment particles suspended in a liquid, called a supernatant, onto a deposition surface, such as a microscope slide. The chamber block includes an inlet orifice communicating with an inlet channel through which a sample of particles suspended in a supernatant is introduced. The inlet channel communicates with an outlet channel that terminates in an outlet orifice. The outlet orifice is disposed in adjacency to the deposition surface. When exposed to a centrifugal force field particles and supernatant move toward the deposition surface where the particles are sedimented thereupon. The chamber block includes a recess preferably in the form of a bore extending therethrough. The bore is adapted to receive an absorbant plug preferably fabricated of porous polyethylene material. The bore extends from rear to front through the block to facilitate manipulation of the plug from the rear of the block. The bore and the plug are preferably tapered over a portion of their length. When received within the bore the tip of the absorbant plug protrudes beyond the chamber block into a contacting relationship against the deposition surface. During centrifugation the centrifugal force imposed on the supernatant overcomes the capillary force exerted by the absorbant material of the plug. As the rotor slows, however, the capillary force becomes dominant thereby drawing the supernatant away from the deposition surface. In the preferred case the outlet orifice and the opening of the bore are both surrounded by a gasket. The bore may be disposed above or below the horizontal centerline of the outlet orifice. Preferably the ratio of area of the outlet orifice to the outlet area at the head of the bore is as large as possible, at least being in the range from ten-to-one to three-to-one.

BRIEF DESCRIPTION OF THE DRAWINGS

The invention will be more fully understood from the following detailed description thereof taken in connection with the accompanying drawings which form a part of this application and in which:

FIG. 1 is a plan view of a rotor member for a centrifuge of the type adapted to deposit particles suspended in a supernatant onto a deposition surface;

FIG. 2 is a side section view of the centrifuge rotor taken along section lines 2—2 of FIG. 1, while FIG. 2A is an isolated perspective view of a deposition surface retaining clip used in connection with the present invention;

FIG. 3 is a side elevation view, entirely in section, of chamber block in accordance with the present invention;

FIGS. 4 and 5 are, respectively, a front elevation and a rear elevation of the chamber block shown in FIG. 3;

FIG. 6 is a side elevation view similar to FIG. 3 showing an alternate embodiment of the chamber block in accordance with the present invention;

FIGS. 7 and 8 are, respectively, front and rear elevational views of the chamber block shown in FIG. 6; and FIG. 9 is an isolated perspective view of an absorbant plug useful with a chamber block shown in FIGS. 3 to 5 or in FIGS. 6 to 8.

DETAILED DESCRIPTION OF THE INVENTION

Throughout the following detailed description similar reference numerals refer to similar elements in all figures of the drawings.

With reference to FIGS. 1 and 2 shown respectively in plan and side section view is a rotor member generally indicated by reference character 10 adapted for use with the chamber block 12 in accordance with the present invention. The rotor 10 includes a bowl 14 fabricated of any suitable material such as steel or plastic. The rotor bowl 14 has a central opening 16 (FIG. 2) which is affixed by any suitable means to a hub 18. The hub 18 is provided with an annular groove 20 in which downwardly depending drive pins 22 are disposed. The groove 20 receives drive pins (not shown) mounted on a rotor gyro which abut against the drive pins 22 in the groove 20 to provide rotational force to the rotor 10 in a manner understood by those skilled in the art.

The inner surface of the side wall of the bowl 14 is provided with flat sections 24 adapted to provide a radially outward support for a deposition surface 26, such as a microscope slide, which is positionable between the chamber block 12 and its corresponding flat section 24 in a manner to be discussed. The deposition surface 26 is held in place on the chamber block 12 by a spring clip 28 (shown in FIG. 2A) although any suitable means of removable attachment of the surface 26 to the block 12 may be used. The lower surface of the bowl 14 contains an annular upward projection 30 arranged to assist in maintaining individual ones of the chamber blocks 12 in position.

As seen in FIG. 2, a lower support plate 32 is mounted to the hub 18 and is secured in place by an adapter 34. The adapter 34 may be threaded or otherwise suitably connected to the hub 18. An upper support plate 38 is mounted atop the adapter 34 and held in position by a cap 40 which is threaded or otherwise affixed to the adapter 34. The peripheral regions of the lower support plate 32 and the upper support plate 38 are each provided with cutout regions 44 (FIG. 1) configured to correspond to the peripheral dimensions of the chamber block 12. The cutout regions 44 in the plates 32 and 38 are in vertical register to define chamber block support openings 46 (FIG. 1) which receive individual chamber blocks 12 and thereby assist in supporting the same in position within the rotor.

The upper edge of the bowl 14 is provided with a recess 47 in which a seal 48 is disposed. A rotor cover 49 having an annular flange 50 is mountable over the bowl 14. The seal 48 laps over the rim of the bowl 14 and is clamped by the flange 50 and the outside of the bowl 14 so that any leakage of supernatant from between the chamber block 12 and the deposition surface 26 is effectively arrested.

As is perhaps best seen in FIG. 2A, the clip 28 is a generally planar member having guide wings 51 sized to engage the sides of the chamber block 12 with which it is associated. Clip arms 52 are bent back to clip onto a convenient surface of the block 12 to thereby secure the deposition surface to the block 12. A viewing aperture 53 is provided in the clip 28 to permit visual inspection of the deposition surface 26 with necessitating removal of the clip. A cutout 54 is provided to facilitate grasping of the deposition surface 26 to permit removal of the clip 28. Corrugations 55 are disposed on the front of the clip 28, preferably extending along the edges thereof. The corrugations 55 abut against the flat section 24 when the clip 28 is secured to the block 12 and the block 12 (with the deposition surface 26 clipped thereto) is inserted into the rotor. The action of the corrugations 55 serves to tilt the block 12 (and deposition surface 26) rearwardly (toward the axis of rotation CL of the rotor) to enhance the supernatant removal action of an absorbent plug P (FIG. 9) insertable into the block 12. Only a slight rearward tilt on the order of two or three degrees (typically 2.3 degrees) is required. Of course any suitable expedient for tilting the block 12 lies within the contemplation of the present invention.

Referring now to FIGS. 3, 4 and 5, various views of a chamber block 12 in accordance with this invention are shown. The chamber block 12 is a generally rectangular member fabricated, as by injection molding, of any suitable material such as a polycarbonate plastic sold by General Electric Co. under the trademark Lexan. The block 12 has an inlet orifice 60 communicating with an inlet channel 62. A well region 64 is disposed at the lower end of the inlet channel 62. The inlet channel 62 communicates with an outlet channel 66 terminating in an outlet orifice 68. The well 64 communicates with the outlet passage 66 over a dam 70 formed in the interior of the chamber block for purpose to be discussed herein.

Extending through the block 12 below the horizontal centerline HCL thereof in a substantially horizontal direction (preferably from the rear surface 72 to the front surface 74 of the block 12) is a bore 76. The bore is preferably cylindrical throughout the majority of its length but is provided with a tapered conical region 78 terminating in a bore head opening 80 disposed in adjacency to the opening of the outlet orifice 68. In the preferred embodiment of the invention the axis of the bore 76 is inclined at a predetermined angle 84 with respect to the axis of the outlet channel 66. The angle 84 lies in the range ten to twenty degrees. In the preferred embodiment the ratio of the area of the outlet orifice 68 taken in a predetermined plane (e.g., a plane parallel to the deposition surface 26) with respect to the area of the head opening 80 of the bore is as large as possible, lying at least within the range from ten-to-one to three-to-one.

A groove 88 is provided in the block 12 and encompasses both the outlet orifice 68 and the head opening 80 of the bore. The groove 88 is provided with a retaining projection 90 arranged to assist in holding a quad seal ring 92 in position within the notch 88. The outlet orifice 68 is connected to the head opening 80 of the bore 76 by a furrow 94 formed in the surface of the block 12.

The chamber block 12 includes two outwardly directed arms 96 terminating in flanges 98 which cooperate to form guide tracks adapted to receive the edges of the deposition surface 26 and to maintain the same in the proper orientation with respect to the chamber block 12 while the block is mounted in the rotor 10. The lateral surfaces of the arms 96 engage the wings 51 of the spring clip 28 (FIG. 2A) while the clip arms 52 engage against the back of the arms 96. A cutout portion 100 is provided near the top of the chamber block 12 to assist in grasping the deposition surface 26 once the clip 28 is removed. An abutment 102 is disposed adjacent the lower end of the block 12 to form a lower stop for the surface 26.

In operation, an absorbant plug P such as shown in FIG. 9, fabricated of a material such as porous polyethylene, is configured to exhibit a cylindrical body B with a tapered end T. Suitable plugs P may be obtained from Chromex Chemical Company, Brooklyn, N.Y., under model number F/N-35-264-7B (G-10 interflow nib). The plug P is insertable through the bore 76 (preferably from the rear of the block) such that the tapered end T of the plug P is received within the tapered portion 78 of the bore with the tip of the plug P projecting through the head opening 80 of the bore 76 to within a predetermined close distance of the deposition surface 26. Preferably the tip of the plug P projects from the block 10 a distance on the order of ten-thousandths of an inch so that the tip of the plug P is placed in a physically contacting relationship with the deposition surface 26.

A sample including cells to be sedimented suspended in a liquid medium known as a supernatant is introduced through the inlet orifice 60 and the inlet channel 62 into the well 64. The dam 70 retains the sample in the well 64 to prevent premature runoff and loss of the sample. When exposed to a centrifugal force field supernatant and cells suspended therein are urged by the centrifugal force field over the dam 70 and move under the influence of the force field through the outlet passage 66 and the outlet orifice 68 to deposit on the surface 26. During rotation the centrifuge force acting in a radially outwardly direction relative to the rotor 10 overcomes the oppositely directed capillary force exerted by the absorbant plug P. However as the rotor slows the capillary force becomes dominant over the centrifugal force and the excess supernatant is withdrawn from the deposition surface leaving only the cells sedimented thereon. The action of the plug P is enhanced due the tilt of the block 12 by the action of the corrugations 55. This causes the supernatant to seek the radially outermost point which lies in the vicinity of the tip of the plug because of the tilt of the block.

With reference to FIGS. 6 through 8 shown is an alternate embodiment of a chamber block 12' in accordance with the invention in which the bore 76 is disposed above the horizontal centerline HCL of the chamber block. In this instance the body of the chamber block 12' is provided with a stepped configuration 108 to accommodate the inlet orifice 60. It is noted that in this embodiment of the chamber block 12' the ratio of the areas of the outlet orifice 68 with respect to the area of the head opening 80 of the bore 76 is as large as possible, at least in the range from ten-to-one to three-to-one. In the embodiment shown in FIGS. 6 through 8 the upward angle of the outlet channel 66 serves as the well 70 to prevent premature runoff of the sample.

Those skilled in the art having benefit of the teachings of the present invention is hereinabove set forth may effect numerous modifications thereto. For example, although the block 12 is shown as having a through bore 76 provided therein which faciliates manipulation of the plug P from the rear of the block 12, any suitable recess (not limited in configuration to a through bore) may be formed within the block 12 to receive a plug of absorbant material. Thus, a recess may be provided which extends partially through the block 12 from the front surface 74 and which is sized to accept a correspondingly configured plug of absorbant material. In addition, it should be noted that the plug P of absorbant material may take any configuration consistent with the configuration of the recess provided in the block. Any configuration of recess and corresponding plug which serves to support the plug within a predetermined close distance of or in a physically contacting relationship with the deposition surface whereby the capillary force of the plug overcomes the centrifugal force field as the rotor slows to collect excess supernatant from the deposition surface lies within the contemplation of the present invention. These and any other modifications are to be construed as lying within the scope of the present invention as defined in the appended claims.

What is claimed is:

1. A chamber block of the type having an inlet channel adapted to receive a sample of cells suspended in a supernatant and an outlet orifice opening on a face of the block through which the cells and supernatant pass under the influence of a centrifugal force field toward a deposition surface, wherein the improvement comprises a recess formed in the chamber block, the recess having an outlet which opens onto the same face as but is spaced from the outlet orifice, the recess having a first predetermined dimension over a first portion of its length which reduces to a lesser dimensioned portion adjacent the end of its length, the recess being sized to receive a plug of an absorbant material itself having a reduced dimensioned portion near an end thereof and to support the reduced dimensioned portion of the plug against the lesser dimensioned portion of the recess such that the end of the plug lies within a predetermined close dimension of the deposition surface.

2. The chamber block of claim 1 wherein the recess comprises a bore that extends through the block from rear to front to facilitate manipulation of a plug from the rear of the block.

3. The chamber block of claim 2 wherein the recess is arranged to support the plug in contacting relationship with the deposition surface.

4. A chamber block of the type having an inlet channel adapted to receive a sample of cells suspended in a supernatant and an outlet orifice opening on a surface of the block through which the cells and supernatant pass under the influence of a centrifugal force field toward a deposition surface wherein the improvement comprises a bore extending through the chamber block, the bore terminating is an opening on the same surface of the block as the outlet orifice, the opening of the bore being spaced from but disposed in proximity to the outlet orifice, the bore having a first predetermined dimension over a first portion of its length which tapers to a lesser dimension adjacent the end of its length, the bore being sized to receive a tapered plug of an absorbant material and to support the tapered plug against the taper of the bore to dispose the plug in contacting relationship with the deposition surface.

5. The chamber block of claim 4 wherein the axis of the bore is disposed below the axis of the outlet orifice.

6. The chamber block of claim 4 wherein the axis of the bore is disposed above the axis of the outlet orifice.

7. The chamber block of claim 5 wherein the ratio of the area of the outlet orifice to the area of the opening of the bore lies within the range from ten-to-one to three-to-one.

8. The chamber block of claim 6 wherein the ratio of the area of the outlet orifice to the area of the opening of the bore lies within the range of ten-to-one to three-to-one.

9. The chamber block of claim 5 wherein a furrow is formed in the surface of the block that connects the outlet orifice and the opening of the bore.

10. The chamber block of claim 6 wherein a furrow is formed in the surface of the block that connects the outlet orifice and the opening of the bore.

11. A centrifuge comprising:
a rotor having a chamber block support opening therein;
a chamber block mounted in the support opening, the chamber block having an inlet channel adapted to receive a sample of cells suspended in a supernatant and an outlet orifice through which the cells and supernatant pass under the influence of a centrifugal force field toward a deposition surface, the chamber block having a recess formed therein, the recess having a first predetermined dimension over a first portion of its length which reduces to a lesser dimensioned portion adjacent the end of its length, the recess terminating in an opening: and an absorbant plug disposed within the recess itself having a reduced dimensioned portion near an end thereof, the recess being sized to receive the plug and to support the reduced dimensioned portion of the plug against the lesser dimensioned portion of recess such that the tip of the plug extends through the opening of the recess into contacting relationship with the deposition surface.

12. The centrifuge of claim 11 wherein the recess comprises a bore that extends through the block from the rear to front to facilitate manipulation of the plug from the rear of the block.

13. The centrifuge of claim 12 wherein the axis of the bore is disposed below the axis of the outlet orifice.

14. The centrifuge of claim 12 wherein the axis of the bore is disposed above the axis of the outlet orifice.

15. The centrifuge of claim 13 wherein the ratio of the area of the outlet orifice to the area of the head of the bore lies within the range from ten-to-one to three-to-one.

16. The centrifuge of claim 14 wherein the ratio of the area of the outlet orifice to the area of the head of the bore lies within the range from ten-to-one to three-to-one.

17. The centrifuge of claim 12 wherein a furrow is formed in the surface of the block that connects the outlet orifice and the opening of the bore.

18. The centrifuge of claim 13 wherein a furrow is formed in the surface of the block that connects the outlet orifice and the opening of the bore.

* * * * *